United States Patent [19]

Harjunmaa

[11] Patent Number: 4,678,326
[45] Date of Patent: Jul. 7, 1987

[54] APPARATUS FOR THE MEASUREMENT OF FLUORESCENCE, TURBIDITY, LUMINESCENCE OR ABSORPTION

[75] Inventor: Hannu Harjunmaa, Espoo, Finland
[73] Assignee: Labsystems Oy, Helsinki, Finland
[21] Appl. No.: 611,132
[22] Filed: May 17, 1984
[30] Foreign Application Priority Data May 30, 1983 [FI] Finland .................................. 831936

[51] Int. Cl.[4] ..................... G01N 21/49; G01N 21/64; G01N 21/59
[52] U.S. Cl. ...................................... 356/73; 250/227; 250/574; 356/317; 356/338; 356/417
[58] Field of Search ............ 250/227, 364, 373, 458.1, 250/461.1, 574, 576; 356/73, 244, 246, 317, 318, 337, 338, 342, 343, 409, 414, 417, 432, 436, 440, 441, 442

[56] References Cited

U.S. PATENT DOCUMENTS 3,068,739 12/1962 Hicks, Jr. et al. ................... 356/342
3,310,680 3/1967 Hasegawa ........................... 356/343

FOREIGN PATENT DOCUMENTS 0047094 3/1982 European Pat. Off. ............. 356/73
0164941 12/1981 Japan ................................... 356/414

OTHER PUBLICATIONS

Durham, III, et al., *IBM Technical Disclosure Bulletin*, v. 18, No. 9, Feb. 1976, p. 2980.

Primary Examiner—F. L. Evans
Attorney, Agent, or Firm—Hopgood, Calimafde, Kalil, Blaustein & Judlowe

[57] ABSTRACT

An apparatus for measuring optical properties such as fluorescence, luminescence or absorption by a liquid sample includes collimating lenses disposed adjacent a cuvette so that their optical axes coincide with the central axis of the cuvette. A fiber bundle with an end portion is located adjacent to the lenses and is provided with a plurality of distinct light transmitting paths extending along the length of the fiber bundle to its end portions. The fiber bundle and collimating lenses cooperate to communicate collimated light between the sample and fiber bundle. The lenses are operable to focus light emanating from the sample upon the end portion of the fiber bundle so that an equal proportion from each volume element of the sample is incident on the fiber bundle surface.

7 Claims, 2 Drawing Figures

APPARATUS FOR THE MEASUREMENT OF FLUORESCENCE, TURBIDITY, LUMINESCENCE OR ABSORPTION

TECHNICAL FIELD

The present invention is concerned with equipment by means of which it is possible to measure fluorescence, turbidity, luminescence, and absorption out of liquid samples.

BACKGROUND ART

In the prior art, several different apparatuses are known for the measurement of the fluorescence, turbidity, luminescence, or absorption of a liquid sample separately. Some systems are also known in which two or more of the measurements mentioned above are combined. In such a case, however, it has not heretofore been possible to achieve the quality of performance with combined measurements as is possible with an apparatus designed specifically for one function only.

In this connection, it is known in the art to make use of the internal total reflection in a cuvette. For example, DE No. 3 122 896 describes an equipment in which light beam goes horizontally through a chamber filled with liquid sample and in which absorbance is measured using total reflection. Vertical photometric measurement is shown e.g. in GB No. 1 486 210.

OBJECTS AND SUMMARY OF INVENTION

An object of the present invention is to provide an apparatus whose performance in all measurements is of the high quality and, in particular in fluorometry, substantially superior to conventional apparatuses.

In an apparatus in accordance with the invention, a sample to be examined is placed in a cuvette which is of cylindrical shape, one of the ends of the cuvette, perpendicular to the axis of the cylinder, being open and directed upwards. The bottom of the cylinder is transparent. The main part of the optics of the apparatus is placed underneath the cuvette. Immediately underneath the cuvette, there is a lens system, to which an optical fibre bundle is rigidly fixed thereto. The centre axis of the cuvette, the optical axis of the lens system and the centre axis of the end of the fibre bundle coincide.

The fibre bundle consists of four zones: a circular central zone, two annular outer zones and an annular intermediate zone between the central zone and the outer zones. The intermediate zone does not contain optical fibres. The central fibre zone guides the light from the light source to the cuvette. The outer zones are used for passing the light coming from the cuvette to one or several light detectors.

The function of the lens system is to collimate the light departing from the central fibre zone so that substantially the whole sample is illuminated by a light beam parallel to the walls of the cuvette. It is another function of the lens system to collect the radiation departing from the area of the cuvette bottom at an angle smaller than a certain critical angle relative the centre axis of the cuvette into the outer fibre zones.

The critical angle mentioned above must be smaller than 61°, calculated from the axis of the cuvette; the maximum light-collecting efficiency is obtained at an angle of 61° as more fully discussed hereinbelow.

Perhaps the most important two advantages of the apparatus in accordance with the invention are that the sample is illuminated uniformly and that an equal proportion of the light radiated by the sample is passed to the detector from each point of the sample. In fluorometry and nephelometry, both of these advantages are essential for the operation of the apparatus. In luminometry, wherein the sample is not illuminated, uniformity of the illumination is unimportant. Thus, in these three modes of measurement, and, in the way known in prior art, in absorption measurement, the well-known advantages of vertical measurement are in force: The result of measurement depends exclusively on the overall quantity of the substance to be measured in the cuvette, and not on the quantity of solvent or on possibly uneven distribution of the substance in the vertical direction of the cuvette; the sensitivity of the measurement can be adjusted by adjusting the quantity of liquid in the cuvette; see e.g. Suovaniemi, O., "Performance and properties of the Finnpipette Analyzer System", Proceedings of the *Second National Meeting on Biophysics and Biotechnology in Finland,* Kairento, A. L., Riihimäki E., and Tarkka, P., Eds., pp. 183–187 (1976), and Suovaniemi, O., Järnefelt, J., "Discrete Multichannel Analysis Systems", *International Laboratory,* April 1982 and *American Laboratory,* June 1982. Moreover the equipment now invented is also well suitable for the measurement of an antibody adhering to microbeads and marked with a fluorescent agent.

BRIEF DESCRIPTION OF DRAWINGS

The invention is discussed in detail below in connection with the figures wherein.

DETAILED DESCRIPTION

Figure 1:
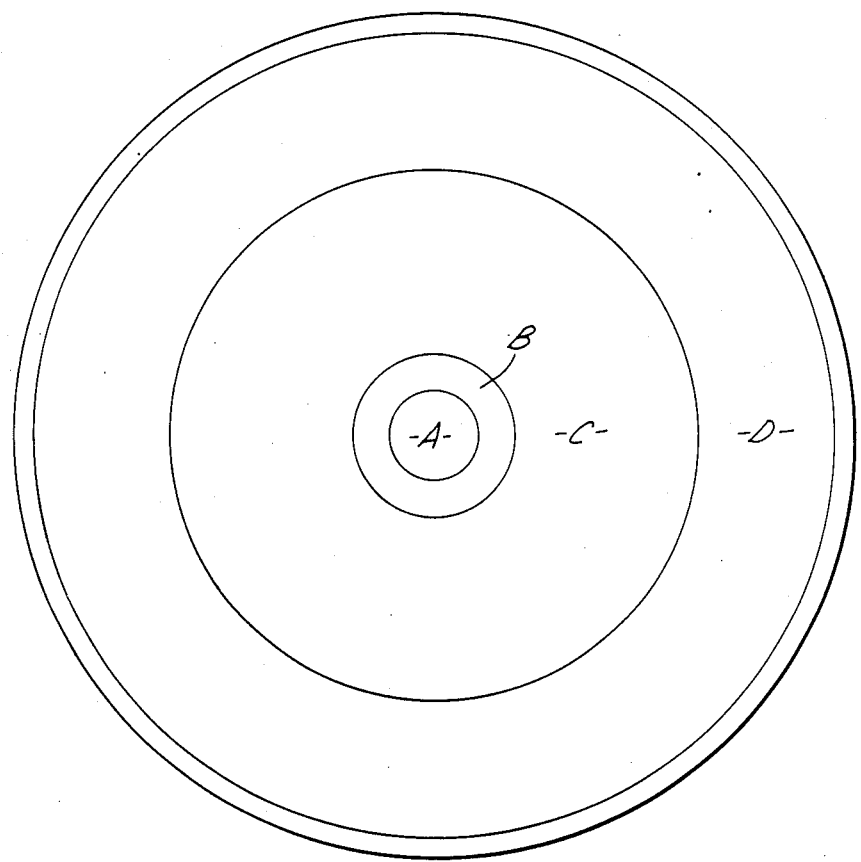
FIG. 1 is a sectional view showing the terminus of the fiber bundle at the point designated 4 in FIG. 2.
Figure 2:
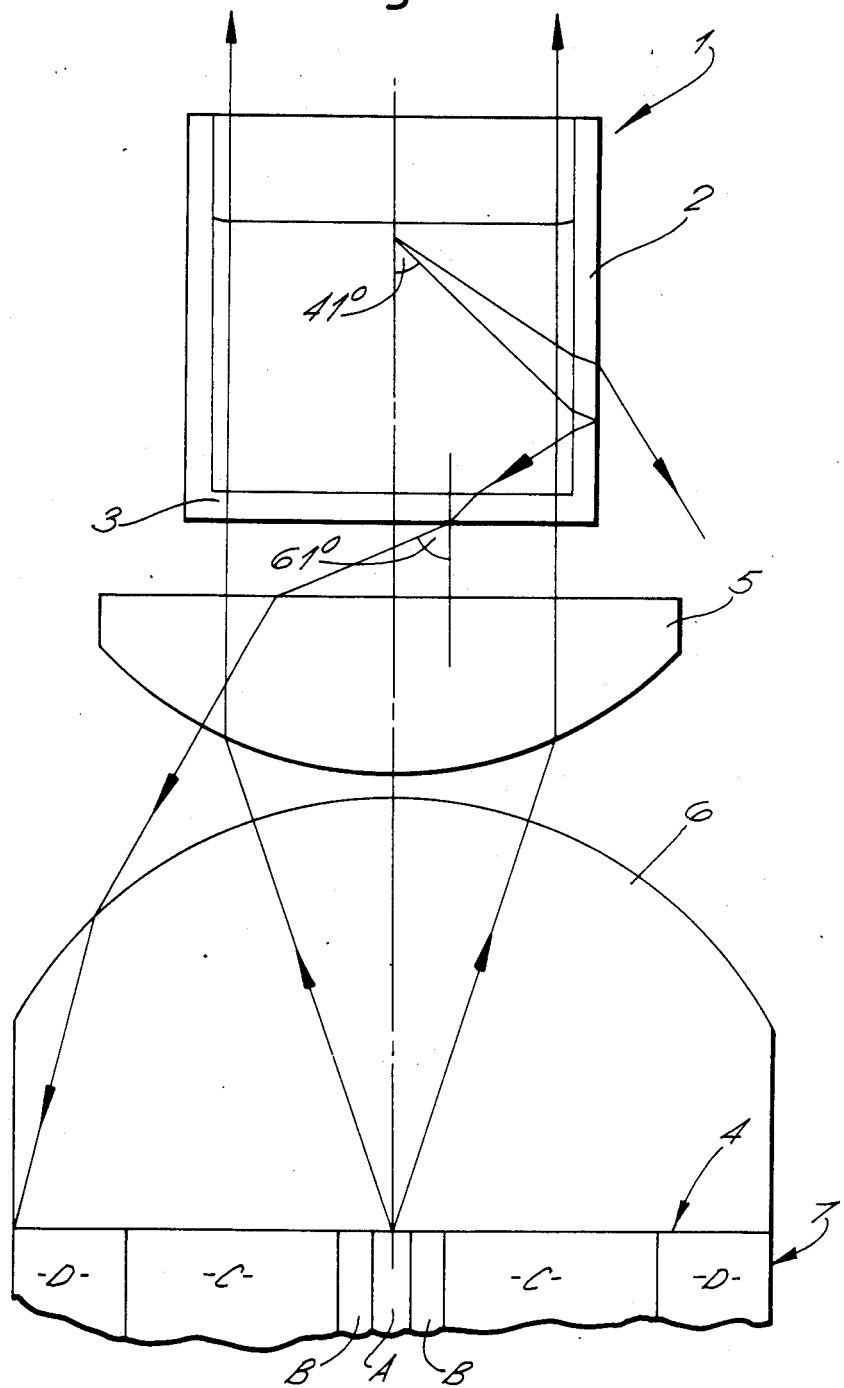
FIG. 2 is a schematic view of the inventive apparatus.

Referring to FIG. 2 the value 61° of the critical angle is shown. Radiation departing from any portion whatsoever of the liquid sample at an angle larger than 41° relative the axis of the cuvette 1 passes out of the cuvette through its side wall 2. Radiation departing at an angle smaller than 41° relative the cuvette axis undergoes reflection inside the cuvette while the absolute value of the directional angle remains unchanged. Now, if the beam of light moving at an angle of 41°, having barely undergone total reflection, meets the bottom 3 of the cuvette, in accordance with Snell's law of refraction, it changes its directional angle so that, in the air space below a plane-bottom cuvette, the angle is 61°. The angle values referred to above are correct when the refractive index of the sample is 1.33. It is to be noticed that, if the wall and the bottom of the cuvette are of uniform thickness, they do not affect the directional angles even if their refractive index were higher than 1.33. Each angle between 0° . . . 61° corresponds to a certain transverse distance from the centre point of the end of the fibre bundle placed in the the common terminal plane of focal plane 4 of the lens system.

In fluorometry, the excitation light passing along the central fibre zone A passes through the plano-convex lenses 5 and 6 and, thereupon, forms a bundle of parallel beams of light, which illuminates the contents in the cuvette uniformly and is limited in such a way that the vertical walls of the cuvette are not illuminated. Some of the excitation light is reflected back from the lens surfaces and from the inner and outer surface of the cuvette bottom as well as from the free surface of the liquid. From the surfaces through which the beam of excitation light passes perpendicularly, the beam is reflected back to its starting point. Since the zone A is not a point-like source of light, some of the reflected light reaches the focal plane outside that zone. The zone B is an intermediate protective zone, whose outer radius is, e.g., three times as long as the radius of zone A. Those beams reflected from the perpendicular surfaces that do not meet the zone A meet the zone B and do not end up in the portion of the fibre bundle 7 from which the emission is measured. If the sample is fluorescent, light of a wavelength longer than the wavelength of the excitation light is emitted from it in all directions. The total reflection taking place from the vertical walls of the cuvette causes that each beam of light whose directional angle inside the sample, as measured from the downward direction of the cuvette axis, is smaller than 41° escapes out of the sample through the cuvette bottom 3. When the beam of light passes out of the sample into the air, its directional angle becomes larger so that the directional angle of a sample whose directional angle in the sample is 41° is 61° in the air. The lenses focus all the beams of light incident thereon when the directional angle is smaller than 61° to the focal plane 4 placed at the end of the fibre bundle. In the focal plane, the emission light passes into the fibres in outer zones C and D, and along these fibres to the light detector.

In luminometry, the sample emits light by the effect of a chemical reaction. The apparatus collects the emitted light and passes it to the light detector exactly in the same way as in fluorometry. Thus, the only difference is that, in luminometry, the source of light is not in operation.

In nephelometry, the light scattered or deviated by the solid particles in the sample is measured. As the source of light in nephelometry, either the same source of light is used as in fluorometry, or a beam of light coming into the cuvette from the top along its centre axis, such as, e.g., a laser beam. In the latter case, having passed through the cuvette and the lens, the beam of light meets the fibre zone A. The scattered light is measured by using the fibre zone D only. Only those beams of light meet that zone whose scattering angle is within the range of $\alpha \ldots 41°$, wherein $\alpha$ is determined by the width of the zone D. Access of light to the light detector along the fibres in zone C must be prevented.

In absorption measurement, there are two possible procedures: the light passing through the sample can be measured either by means of a light detector placed above the cuvette, or by means of the same light detector as in the other modes of measurement. In the latter case, a light-reflecting surface must be placed above the cuvette, which said surface should be preferably dull white or retroreflecting.

The equipment may include a detachable cuvette set and a separate optical system for each cuvette.

In the example discussed the walls of the cylinder are transparent, but they may also be light-reflecting. The light may also be collected for detection entirely without lenses, because an optical fibre also has a critical angle of its own, whereat beams of light arriving at an angle larger than that critical angle do not propagate in the fibre. The cuvette bottom may also, if it is appropriately shaped, function as a lens performing these two functions.

The equipment may also include, in a way in itself known, a second light detector, to which the light is passed directly from the light source. Then the equipment may include a beam switch which switches the light from the source of light so that it passes alternatingly along the path of light passing to the cuvette and alternatingly along the path of light passing straight to the reference light detector. The beam switch may be a three-position beam switch which, in its first position, makes the light from the source of light pass along the path of light passing to the cuvette, in the second position along the path of light passing straight to the reference light detector, and in the third position prevents access of light to any of the paths of light. The alternating takes place asymmetrically so that the path of light passing from the source of light to the cuvette is open most of the time.

What is claimed is:

1. In an apparatus for measuring optical properties such as fluorescence, luminescence, turbidity and absorption of a liquid sample contained in a cylindrical cuvette having a central optical axis, the apparatus including a light source and at least one light sensor, the apparatus further comprising collimating means disposed adjacent said cuvette, the collimating means having an optical axis in alignment with both the central optical axis of the cuvette and a central optical axis of a fiber bundle, said fiber bundle having an end portion located adjacent to said collimating means and defining a plurality of independent light transmitting paths, said light transmitting paths extending along the length of said fiber bundle to its end portions, wherein said fiber bundle and collimating means transmit collimated light to said sample and selectively collect light emanating therefrom, said collimating means having at least one lens means to focus light emanating from said sample upon the end portion of said fiber bundle adjacent thereto whereby a substantially equal proportion of light from a volume element of said sample is transmitted to said fiber bundle by way of said collimating means.

2. The combination according to claim 1, wherein said collimating means is located underneath said cuvette and said fiber bundle is fixedly attached to said collimating means.

3. The combination according to claim 1, wherein said independent light paths of said fiber bundle are concentrically arranged and include at least two light-conducting channels separated by a substantially opaque annulus.

4. The combination according to claim 3, wherein said light conducting channels of said fiber bundle terminate in a common plane adjacent said collimating means.

5. The combination according to claim 1, wherein said collimating means comprises two plano-convex lenses arranged underneath said cuvette with their convex surfaces in opposed facing relation to one another.

6. The combination according to claim 2, wherein said collimating means comprises two plano-convex lenses arranged underneath said cuvette with their convex surfaces in opposed facing relation to one another.

7. The combination according to claim 1, wherein said collimating means includes a pair of plano-convex lenses arranged underneath said cuvette with their convex surfaces in opposed facing relation and said fiber bundle includes at least two light conducting channels separated by a substantially opaque annulus.

* * * * *